United States Patent [19]

Adair

[11] Patent Number: 5,311,858

[45] Date of Patent: May 17, 1994

[54] IMAGING TISSUE OR STONE REMOVAL BASKET

[76] Inventor: Edwin L. Adair, 317 Paragon Way, Castle Pines Village, Colo. 80104

[21] Appl. No.: 898,311

[22] Filed: Jun. 15, 1992

[51] Int. Cl.$^5$ .............................................. A61B 1/00
[52] U.S. Cl. ...................................... 128/4; 606/127; 128/6
[58] Field of Search ............... 128/4, 6; 606/110, 113, 606/114, 127, 128, 159

[56] References Cited

U.S. PATENT DOCUMENTS

| | | | |
|---|---|---|---|
| 4,046,150 | 9/1977 | Schwartz et al. | 606/127 |
| 4,069,149 | 9/1977 | Komiya . | |
| 4,198,960 | 4/1980 | Utsugi . | |
| 4,471,766 | 9/1984 | Terayama | 128/6 |
| 4,557,255 | 12/1985 | Goodman | 606/127 X |
| 4,590,938 | 5/1986 | Segura et al. . | |
| 4,718,419 | 1/1988 | Okada . | |
| 4,741,335 | 5/1988 | Okada | 606/127 |
| 4,759,348 | 7/1988 | Cawood | 128/6 |
| 4,791,913 | 12/1988 | Maloney | 128/6 |
| 4,848,323 | 7/1989 | Marijnissen et al. | 128/6 |
| 4,994,079 | 2/1991 | Genese et al. | 128/6 X |
| 5,059,199 | 10/1991 | Okada et al. . | |
| 5,074,867 | 12/1991 | Wilk . | |
| 5,084,054 | 1/1992 | Bencini et al. . | |
| 5,176,688 | 1/1993 | Narayan et al. | 606/127 X |
| 5,192,291 | 3/1993 | Pannek, Jr. | 606/170 X |

FOREIGN PATENT DOCUMENTS 278958  8/1970  U.S.S.R. .

Primary Examiner—Richard J. Apley
Assistant Examiner—Karen A. Jalbert
Attorney, Agent, or Firm—Fields, Lewis, Pittenger & Rost

[57] ABSTRACT

In accordance with this invention, an endoscope is provided which has an imaging tissue or stone removal basket for removal of unwanted tissue or stone from an operative site, such as a body passageway or cavity. The endoscope includes an elongated tube, having a distal end and a proximal end. An elongated basket having a circular distal end with a central opening therein and a proximal end which is attached to the periphery of the distal end of the tube is provided. The basket is formed as a plurality of spaced flexible members which normally bow outwardly between the distal end and the proximal end of the basket. An optic fiber bundle is slidably received within the tube and is of smaller diameter than the tube. Structure is provided for selectively adjusting the optic fiber bundle along the tube so that the distal end of the bundle is selectively located from a position within the circular distal end of the basket to a position at the distal end of the tube. Structure is also provided for introducing fluid under pressure through the tube from the proximal@end thereof to the distal end. The fluid flows around the optic fiber bundle to the distal end of the tube for improving visibility of the operative site. Also, the fluid under pressure can be used for dislodging unwanted tissue or stone.

6 Claims, 2 Drawing Sheets

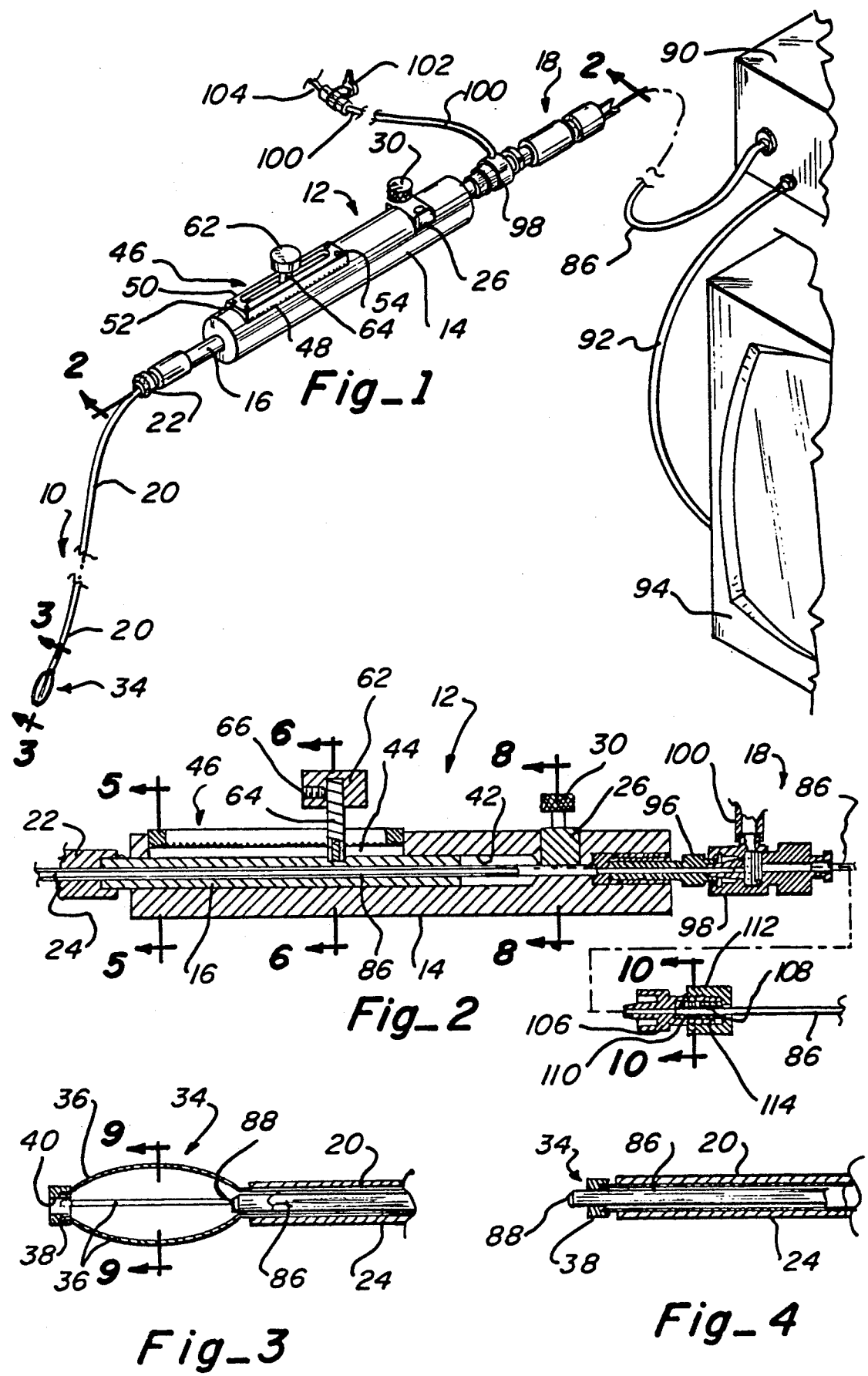

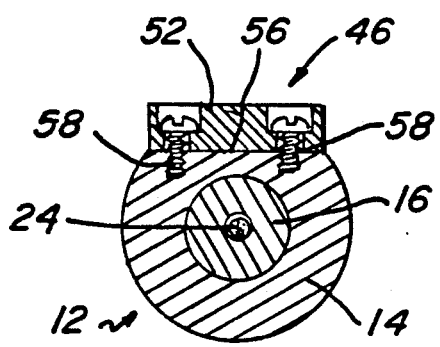
Fig_5
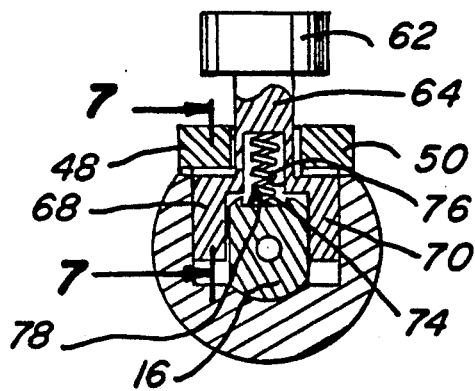
Fig_6
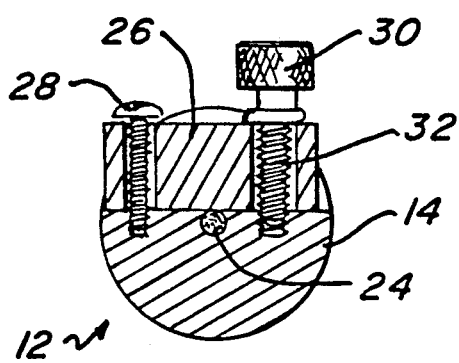
Fig_8
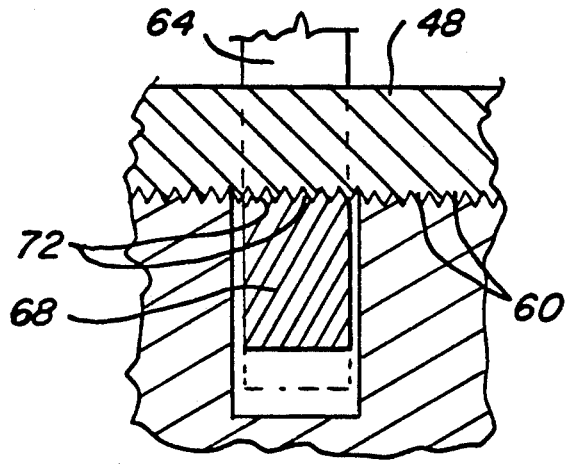
Fig_7
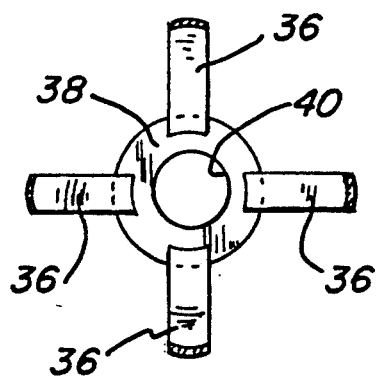
Fig_9
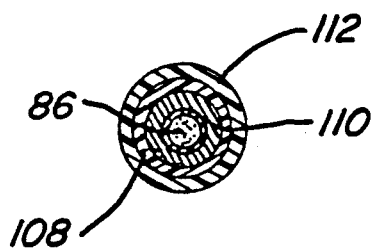
Fig_10

IMAGING TISSUE OR STONE REMOVAL BASKET

TECHNICAL FIELD

This invention relates to an extracting basket and more particularly to a tissue or stone removal or stone extracting basket which includes means for viewing the tissue or stone to be removed and for providing fluid under pressure to assist in viewing and removal of the unwanted tissue or stone.

BACKGROUND ART

Tissue or stone extracting baskets have been available for several decades. For the most part, these devices are used blind in that the grasping of the stone is done by the feel of the surgeon rather than by visual observation. In gastroenterology, the basket may be passed down the working channel of the large endoscope such as a gastroduodenoscope. The basket is controlled under direct vision provided by the larger endoscope.

In case of very small internal channels, such as the human ureter and the human salivary gland duct or the cystic duct, the very small diameter of the channel makes it impossible to visually observe what is happening by use of current technology.

U.S. Pat. No. 4,046,149 to Komiya discloses an endoscope having a basket which can be retracted inside the sleeve. Optical means is provided in the endoscope above the sleeve.

U.S. Pat. No. 4,198,960 to Utsugi discloses an endoscope having a basket with individually retractable arms. The center of the endoscope is provided with a central passageway which can be used for viewing optics and illumination fibers, or these can be withdrawn for insertion of liquid injecting means or vacuum means.

U.S. Pat. No. 4,590,938 to Sequra et al. discloses a stone basket having a plurality of spring arms which are extendable for use and retractable within a sleeve during insertion.

U.S. Pat. No. 4,718,419 to Okada discloses an endoscope with a snare on the end thereof which can be partially drawn inside of a tubular member to reduce its size or pushed outside of the tube to enlarge its size. It has a handle assembly with a series of notches and set screw so that the adjustment of the size of the snare can be made incrementally and the device held in the appropriate position by the set screw.

Russian Patent No. 278,958 discloses an endoscope having a basket and optics within a tubular member.

U.S. Pat. No. 5,074,867 to Wilk, shows in FIG. 2F, an endoscope device for use with a collapsible membrane, having both a laser source and light source.

U.S. Pat. No. 5,059,199 to Okada et al.discloses an endoscope with a basket which can be extended or withdrawn into a sleeve.

U.S. Pat. No. 5,084,054 discloses a surgical gripping instrument having a loop which can be drawn into a tubular member.

DISCLOSURE OF THE INVENTION

In accordance with this invention, an endoscope is provided which has an imaging tissue or stone removal basket for removal of unwanted tissue or stone from an operative site, such as a body passageway or cavity. The endoscope includes an elongated tube, having a distal end and a proximal end. An elongated basket having a circular distal end with a central opening therein and a proximal end which is attached to the periphery of the distal end of the tube is provided. The basket is formed as a plurality of spaced flexible members which normally bow outwardly between the distal end and the proximal end of the basket. An optic fiber bundle is slidably received within the tube and is of smaller diameter than the tube. Means is provided for selectively adjusting the optic fiber bundle along the tube so that the distal end of the bundle is selectively located from a position within the circular distal end of the basket to a position at the distal end of the tube. Means is also provided for introducing fluid under pressure through the tube from the proximal end thereof to the distal end. This fluid flows around the optic fiber bundle to the distal end of the tube for improving visibility of the operative site. Also, the fluid under pressure can be used for dislodging unwanted tissue or stone.

More particularly, the endoscope can include a sleeve slidably received over the tube which is adjustably positioned along the tube from a position where the distal end of the sleeve is substantially coterminous with the distal end of the basket to enclose the same and a position where the distal end of the sleeve is substantially coterminous with the distal end of the tube to expose the basket.

Conveniently, an elongated handle is provided with a slidable arm therein which is releasably connected to the sleeve for positioning the sleeve over the basket as desired. The optic bundle extends centrally through the arm and has a diameter substantially smaller than the inner diameter of the arm. A slidable control means is provided on the handle and is connected to the arm for extending and retracting the arm with respect to the distal end of the handle to extend and retract the sleeve. A clamping means is provided intermediate the ends of the handle for releasably holding the proximal end of the tube in a fixed position relative to the handle. The slidable control means comprises a longitudinal opening extending through the handle and a rack extending along each side of the opening. A shaft extends through the slot from the arm and has a pair of spaced shoulder gripping means which are engageable with the respective racks when the shaft is spring urged to an extended position. A knob is attached to the outer end of the shaft for depressing the shaft and the shoulders against the force of the spring to extend and retract the arm with respect to the handle.

Conveniently, a fitting is releasably connected to the proximal end of the handle with the optical bundle passing therethrough. The fitting has means for selectively introducing fluid under pressure into the tube around the optic fiber bundle for discharge through the distal end of the tube. A fluid tight means is provided for adjustably positioning the optical fiber bundle longitudinally with respect to the tube. This fluid tight means comprises a O-ring seated in the fitting with the optical fiber bundle extending therethrough. An adjustable annular member is provided for applying pressure to the O-ring about is periphery to urge the inner surface thereof into sealing engagement with the optic fiber bundle.

The invention also contemplates a method of removing unwanted tissue or stone from a body passage which includes the steps of inserting an endoscope of the type previously described into a bodily passageway to position the distal end of the endoscope at the operative site.

Unwanted tissue or stone is located by viewing the image through the optic bundle. The unwanted tissue or stone may be blasted by the fluid under pressure to dislodge it. Alternatively, the unwanted tissue or stone can be captured within the basket and the basket rotated so that one of the flexible members cuts the unwanted tissue or stone from the operative site. The sleeve can then be extended partially over the basket to draw the flexible members tightly around the unwanted tissue or stone to firmly grip it while the endoscope is removed from the passageway so to dispose of the unwanted tissue or stone.

Alternatively, the basket can be rotated to morselate the unwanted tissue or stone which can then be blasted with fluid under pressure to remove it from the operative site. In some instances, the end of the basket can be used to dislodge the unwanted tissue or stone which can then be pushed out of the passageway by the high pressure fluid. Additional advantages of this invention will become apparent from the description which follows, taken in conjunction with the accompanying drawings.

BRIEF DESCRIPTION OF THE DRAWINGS

FIG. 1 is a perspective view of an endoscope constructed in accordance with this invention;

FIG. 2 is a longitudinal section, on an enlarged scale, taken along line 2—2 of FIG. 1, showing the internal construction of the endoscope;

FIG. 3 is an enlarged longitudinal section, taken along line 3—3 of FIG. 1, showing the sleeve retracted from the basket;

FIG. 4 is a longitudinal section, similar to FIG. 3, but showing the sleeve extending over the basket;

FIG. 5 is an enlarged vertical section, taken along line 5—5 of FIG. 2, showing the attachment of the rack to the handle;

FIG. 6 is an enlarged vertical section taken along line 6—6 of FIG. 2, showing details of the control knob;

FIG. 7 is a greatly enlarged vertical section, taken along line 7—7 of FIG. 6, showing the rack engaging means;

FIG. 8 is an enlarged vertical section, taken along line 8—8 of FIG. 2, showing the clamping means for the tube;

FIG. 9 is an enlarged vertical section, taken along line 9—9 of FIG. 3, showing further details of the basket; and FIG. 10 is an enlarged vertical section, taken along line 10—10 of FIG. 2, showing the O-ring sealing structure.

BEST MODE FOR CARRYING OUT THE INVENTION

In accordance with this invention, an endoscope 10 is provided which has an elongated handle 12. Handle 12 includes an elongated hollow body 14, having an arm 16 slidably extendable from the distal end thereof and having a fitting 18 attached to the proximal end thereof. A flexible tube 20 is connected to the distal end of arm 16 by a releasable connector 22, such as a luer lock. Within body 14 is a flexible tube 24 whose proximal end extends through arm 16 and is held in adjustably fixed position by means of clamp bar 26, as best seen in FIGS. 2 and 8. One side of clamp bar 26 is held loosely in position, as by rivet 28. The other side of clamp bar 26 is releasably clamped by means of threaded knob 30 having a shaft 32 threadably received in body 14 of handle 12. Thus, to attach endoscope 10 to handle 12 it is merely necessary to insert tube 24 into the end of the handle so that the proximal end thereof is positioned under clamp bar 26 whereupon knob 30 is tightened to hold it in place. The sleeve 20 is then attached to the end of arm 16 by releasable connector 22. To remove the endoscope from the handle, the releasable lock 22 is disconnected, knob 30 is loosened so as to release clamp bar 26.

Connected to the end of flexible tube 24 is a tissue or stone removal basket 34 which includes a plurality of spaced outwardly bowed flexible members 36, connected at one end to the distal end of tube 24 and connected at the other end to a circular ring 38 which has a central opening 40, best seen in FIGS. 3 and 9. During insertion into the-body passageway, the sleeve 20 will be extended over the basket 34 as shown in FIG. 4. During this operation, arm 16 of handle 12 will be extended. After insertion, handle 16 will be retracted which will pull sleeve 20 back from the basket so that it is exposed as shown in FIG. 3 for engaging unwanted tissue or stone, such as a gall stone or kidney stone, all as will be more fully described below.

As best seen in FIG. 2, arm 16 is slidable within handle body 14 within cylindrical passageway 42. The upper portion of handle body 14 has a longitudinal opening 44 to which a rack assembly 46 is attached. Rack assembly 46 is generally rectangular in shape having two longitudinal members 48 and 50 interconnected by cross members 52 and 54. The portion around opening 44 is cut away to form a flat surface 56, shown in FIG. 5, upon which rack assembly 46 rests. The rack assembly is held in place by suitable fastening means, such as screws 58, also shown in FIG. 5. As best seen in FIG. 7, the bottom portion of side members 48 and 50 have serrations or teeth 60 forming racks along opposite sides of rack assembly 46.

A control knob 62 is attached to a post 64, as by set screws 66, shown in FIG. 2. As best seen in FIG. 6, post 64 is connected to and vertically movable with shoulder members 68 and 70 which include mating serrations or teeth 72, as best seen in FIG. 7. The shoulder members 68 and 70 and control knob and post 64 are urged upwardly by resilient means, such as coil spring 74 provided in a recess 76 in post 74. Thus, as seen in FIG. 6, one end of the coil spring bears against the end of recess 76 and the other end of the coil spring bears against a flat surface 78 on arm 16.

From the foregoing, it should be apparent that by selectively depressing control knob 62 and pushing forward or backward with respect to handle body 14, the flexible sleeve 20 connected to arm 16 will be moved forwardly over basket 34 as shown in FIG. 4 or retracted therefrom when the knob is depressed and pulled rearwardly to expose the basket, as shown in FIG. 3. With the incremental adjustment feature provided by rack assembly 46 and shoulder members 68 and 70, respectively, incremental adjustments can be made so that the basket is only partially exposed to the extent required for any particular surgical procedure.

An optic fiber bundle 86 having a much smaller diameter than flexible tube 24 extends through the center thereof and has a distal end 86, as shown in FIG. 3, which extends just beyond the end of tube 20. The proximal end of optic fiber bundle 86 extends through fitting 18 and is connected to an image processing unit 90 which is connected through a conduit 92 to a video monitor 94. The image processing unit can be provided with a light source which transmits light to the operating site through some of the fibers of optic fiber bundle 86. The remaining fibers transmit the image back to imaging processing unit 90 which, through conduit 92, projects an image on video monitor 94 for the surgeon to view the operative site. A suitable optical bundle is shown in my U.S. Pat. No. 4,782,819, for "Optical Catheter".

Fitting 18 is releasably attached to a connector 96, such as a luer lock, secured to the proximate end of handle body 14, as best seen in FIG. 2. Fitting 18 includes a fluid connection 98 through which fluid under pressure is introduced into the space around optic fiber bundle 86 by means of fluid tube 100. The flow of fluid is controlled by valve 102 which is connected to a source of fluid through conduit 104. Fluid, thus introduced, travels through tube 24 around optic fiber bundle 86 And is projected out the distal end thereof under pressure to clear the operative site for viewing through the optic fiber bundle and for blasting and dislodging unwanted tissue or stone to move it from the operative site. The proximal end of fitting 18 is provided with a connector 106 having a recess 108 which receives an O-ring 110 surrounding optic fiber bundle 86. As seen in FIGS. 2 and 10, a cap 112 is threadably received on connector 106 and has an annular member in the form of pressure sleeve 114 which projects into recess 106 and applies pressure to O-ring 110 as the cap is tightened to expand the O-ring inwardly against optic fiber bundle 86 to create a fluid tight seal so that fluid supplied through tube 100 does not escape through cap 112.

In use, the endoscope 10 is introduced into proximity to an operative site through a body passageway with sleeve 20 extended over basket 34 and optic fiber bundle 86 positioned as shown in FIG. 4. Thus, the surgeon can observe the position of the distal end of the endoscope as it is inserted. When the surgeon sees that it has reached the desired location, the surgeon can view the unwanted body tissue or stone on video monitor 94. Under some circumstances the unwanted tissue or stone can be physically dislodged by pushing the distal end of the endoscope against it to separate it from the operative site. Under other circumstances, the unwanted body tissue or stone can be removed by opening valve 102 to introduce fluid under pressure which is projected through tube 24 for blasting the unwanted body tissue or stone thereby dislodging it from the operative site. Then it can be captured in the basket for removal or forced by the fluid into a larger body cavity where it will be eliminated through normal body functions. In other circumstances, the sleeve 20 will be retracted by manipulation of control knob 62, as previously described, to expose basket 34 so that the unwanted tissue or stone can be trapped between flexible members 36. The basket can be rotated so that these flexible members have the effect of cutting the unwanted tissue or stone from the passageway. Advantageously, during this procedure, the surgeon can view the operative site on video monitor 94 because the distal end 88 of optical fiber bundle 86 is positioned at the proximal end of the basket so that the activity occurring in the basket can be observed. Once the unwanted body tissue or stone has been dislodged, the sleeve 20 is partially extended so as to constrain flexible members 86 to draw them tightly about the unwanted body tissue or stone. Then the endoscope is removed with the body tissue or stone captured in basket 34.

Where the unwanted body tissue or stone is quite large, the basket 13 can be rotated and used as a morselator so that flexible members 36 become cutting blades which cut the unwanted body tissue or stone into small portions which can be discharged by blasting them with the high pressure fluid to move them into a larger body cavity for elimination by natural means or they can be captured in the basket 34, as previously disclosed and removed.

From the foregoing, the advantages of this invention are readily apparent. An endoscope has been provided which is very versatile. In one arrangement, its viewing means are positioned at the distal end of the basket for viewing as the endoscope is introduced into a body passageway, so that it can be accurately positioned at the operative site. In another arrangement, its viewing means is positioned at the proximal end of the basket for viewing the tissue or stone removal basket as it is being manipulated by the surgeon. By this procedure unwanted body tissue or stone can be separated from the wall of the operative site and discharged by blasting with high pressure fluid into a larger body cavity or by withdrawing the separated or morselated tissue or stone by capturing it within the imaging basket. Also, the distal end of the imaging basket can be used to physically dislodge the unwanted tissue or stone by pushing against it and separating it from the wall of the operative site.

This invention has been described in detail with reference to a particular embodiment thereof, but it will be understood that various other modifications can be effected within the spirit and scope of this invention.

I claim:

1. An endoscope having an imaging tissue or stone removal basket for removal of unwanted tissue or stone from an operative site within a body, said endoscope comprising:

an elongated tube, having a distal end and a proximal end;

an elongated basket, having generally circular distal end with a central opening therein and a proximal end, said proximal end of said basket being attached to the periphery of said distal end of said tube, said basket being formed as a plurality of spaced flexible members which normally bow outwardly between said distal end and said proximal end thereof;

an optic fiber bundle slidably received within said tube, said optic fiber bundle having a distal end and a proximal end and a smaller diameter than said tube;

an elongated handle having a distal end, a proximal end and a central passageway therethrough whose diameter is substantially greater than the diameter of said optic fiber bundle;

a sleeve slidably received over said tube, having a distal end and a proximal end;

a slidable tubular arm having a distal end and a proximal end, within said passageway, said distal end thereof projecting beyond said distal end of said handle, releasably connectable to said proximal end of said sleeve, said optic fiber bundle extending centrally through said arm within said passageway and having a diameter substantially smaller than the inner diameter of said arm;

slidable control means on said handle connected to said arm for extending and retracting said arm with respect to said distal end of said handle to extend and retract said distal end of said sleeve with respect to said basket; and clamping means intermediate said ends of said handle for releasably holding said proximal end of said tube in a fixed position relative to said handle.

2. An endoscope, as claimed in claim 1, further including:
   a fitting releasably connected to said proximal end of said handle, said optic fiber bundle passing therethrough, said fitting having means for selectively introducing fluid under pressure into said tube and around said optic fiber bundle for discharge through said distal end of said tube; and
   fluid-tight means for adjustably positioning said optic fiber bundle longitudinally with respect to said tube.

3. An endoscope, as claimed in claim 2, wherein said means for selectively introducing fluid comprises:
   a fluid tube in fluid communication with said fitting, said fluid tube having an inlet for attachment to a source of fluid; and
   a shut-off valve in said fluid tube to control the flow of fluid to said fitting.

4. An endoscope, as claimed in claim 2, wherein said fluid-tight means comprises:
   an O-ring seated in said fitting with said optic fiber bundle extending therethrough; and
   an adjustable annular member for applying pressure to said O-ring about its periphery to urge the inner surface thereof into sealing engagement with said optic fiber bundle.

5. An endoscope, as claimed in claim 3, wherein said slidable control means includes:
   a longitudinal opening extending through said handle, having a longitudinal surface along each side thereof;
   a rack extending along each of said longitudinal surfaces forming a slot therebetween, each rack having teeth facing into said opening;
   a shaft extending through said slot having a first end connected to said arm and having a pair of spaced shoulders, each shoulder having respective gripping means facing each of said respective racks and engageable with said respective racks when said shaft is in an extended position and releasable from said respective racks when said shaft is moved toward said arm to a depressed position, said shaft having a second end extending exteriorly of said handle;
   a knob attached to said second end of said shaft for depressing said shaft and said shoulders to extend and retract said arm with respect to said handle; and
   means resiliently biasing said shaft and said shoulders toward said rack.

6. An endoscope, as claimed in claim 5, further including:
   a sleeve slidably received over said tube, having a distal end and a proximal end; and
   means releasably connecting said proximal end of said sleeve to said slidable arm, said basket and said longitudinally opening being substantially the same length so that when said arm is fully extended said sleeve extends completely over said basket and when said arm is fully retracted said sleeve is completely retracted from said basket.

* * * * *